United States Patent [19]

Bruck et al.

[11] 4,131,800

[45] Dec. 26, 1978

[54] METHOD OF AND APPARATUS FOR DIFFERENTIATING BETWEEN NORMAL AND MALIGNANT CELLS

[75] Inventors: Abraham Bruck, Haifa; Michael Inbar, Rehovot, both of Israel

[73] Assignee: Elscint Ltd., Haifa, Israel

[21] Appl. No.: 774,215

[22] Filed: Mar. 3, 1977

[30] Foreign Application Priority Data

Jun. 13, 1976 [IL] Israel .................................. 48776

[51] Int. Cl.² .......................................... G01N 21/38
[52] U.S. Cl. ............................................... 250/461 B
[58] Field of Search .................................... 250/461 B

[56] References Cited

U.S. PATENT DOCUMENTS 3,887,812  6/1975  Hirschfeld ................... 250/461 B X
3,971,952  7/1976  Inbar et al. ....................... 250/461 B Primary Examiner—Davis L. Willis
Attorney, Agent, or Firm—Donald M. Sandler

[57] ABSTRACT

The normality of a cell labelled with a lipid soluble fluorescent dye and excited with a beam of polarized light can be evaluated by measuring the time dependence of the state of polarization of fluorescence emitted by the cell which is determined by simultaneously measuring the intensities of fluorescence polarized in directions parallel and perpendicular to the direction of polarization of the excitation beam.

The state of polarization of a cell changes markedly as a function of excitation time when the cell is abnormal (i.e., malignant), while the state of polarization of a cell remains substantially constant when the cell is normal. Classification of cells in a population by way of the stability of the state of polarization provides guidance in determining the presence of malignancy in the population.

17 Claims, 1 Drawing Figure

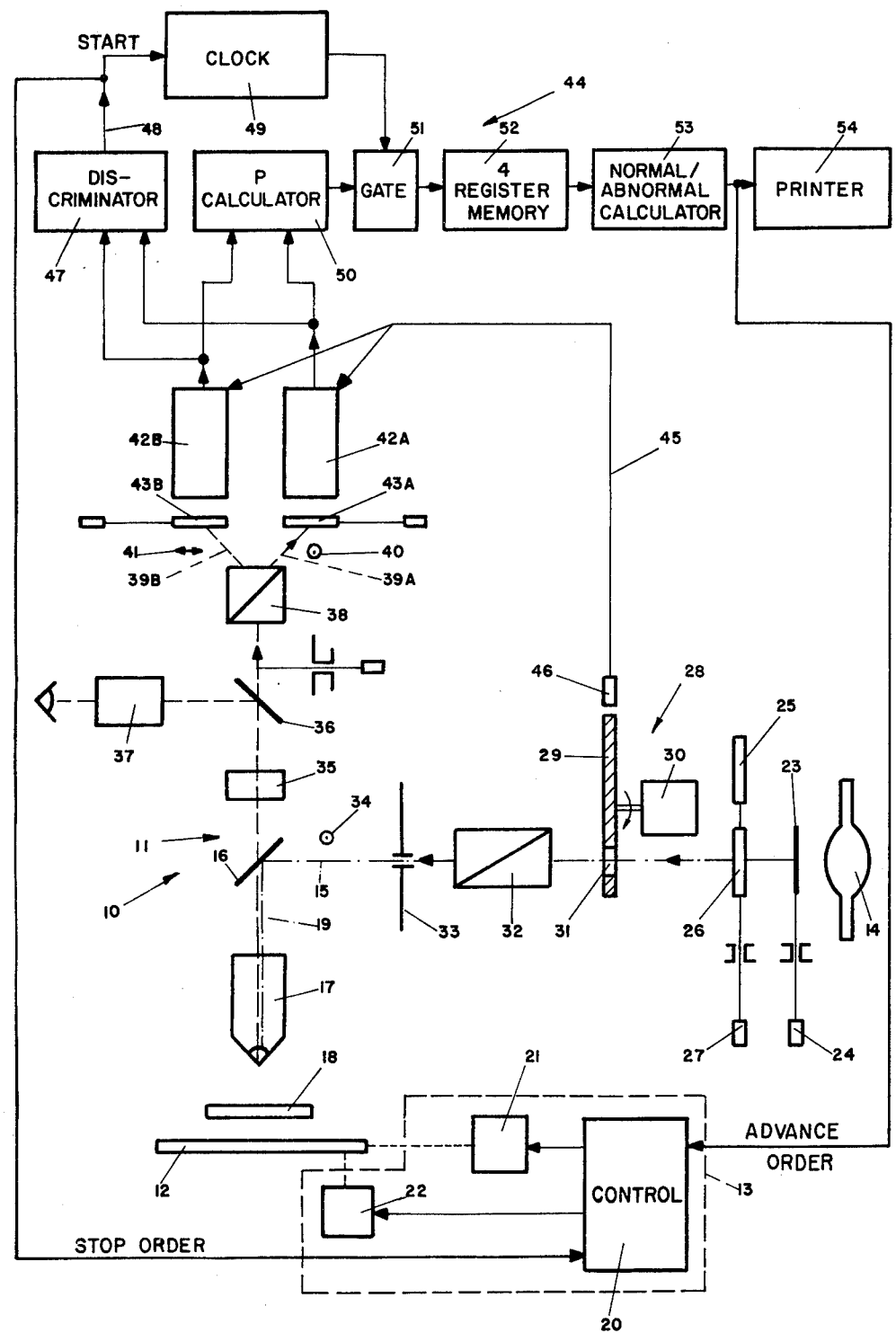

METHOD OF AND APPARATUS FOR DIFFERENTIATING BETWEEN NORMAL AND MALIGNANT CELLS

CROSS-REFERENCE TO RELATED ARTICLES AND PATENTS (1) Copending patent application Ser. No. 782,320 filed Mar. 29, 1977 by Abraham Bruck entitled "Method and Apparatus for Cell-by-Cell Classification of Biological Cells"

(2) U.S. Pat. No. 3,971,952 entitled "Method of Detecting Abnormal Behavior of Mammalian Cells" issued to Inbar et al (3) Shinitsky, M.; Dianoux, A. C.; Gitler, C.; Weber, G.: "Microviscosity and Order in the Hydrocarbon Region of Micelles and Membrances Determined with Fluorescent Probes. I. Synthetic Micells:, *Biochemistry*, Vol. 10, No. 11, pp 2106–2113 (1971)

(4) Von Sengbusch, G. and Thaer, A., "Some Aspects of Instrumentation and Methods as Applied to Fluorometry at the Microscale", 31–39 (Germany)

(5) U.S. Pat. No. 3,699,336 entitled "Biological Cell Analyzing System" issued to Ehrlich et al

BACKGROUND OF THE INVENTION

This invention relates to a method of and apparatus for determining the normality of mammalian cells.

Reference (1), which is hereby incporporated by reference, discloses an improved method of and means for determining the normality of a cell utilizing the state of polarization of the fluorescence emitted by the cell when excited by polarized light. Such fluorescence is, itself, polarized; and the state of polarization of the fluorescence is determined simultaneously by measuring the intensities of fluorescence polarized in directions parallel and perpendicular to the direction of polarization of the excitation light. An analytical combination of the intensities determines the state of fluorescent polarization in terms of fluidity, degree of fluorescent polarization, microviscosity, etc. Reference (2) identifies a number of analytical combinations of intensities.

The state of fluorescent polarization of an individual cell depends on the nature of the cell's plasma membrane. Classification of cells by the distribution of the state of fluorescent polarization provides guidance in determining the presence of malignancy in biological cells.

It is an object of the present invention to provide a new and improved method of an apparatus for determining the normality of biological cells.

SUMMARY OF THE INVENTION

The present invention provides a method for determining the normality of a biological cell that has been labeled with a lipid soluble fluorescent dye and excited with a beam of polarized light by ascertaining the stability of the state of polarization of fluorescence emitted by the cell as a function of excitation time. The state of fluorescent polarization is determined by simultaneous measurement of the intensities of fluorescence polarized in directions parallel and perpendicular to the direction of polarization of the excitation beam; and the time dependency of the state of fluorescent polarization is obtained by making a plurality of sequential measurements.

It has been found experimentally that the degree of fluorescent polarization (which is the ratio of the difference to the sum of the measured intensities) of a malignant cell changes markedly as a function of the excitation time within a period of about 20 seconds, while the degree of fluorescent polarization of a normal cell remains almost constant with time. These observations were obtained with cells from both experimental animals and humans. Identification of a cell whose degree of fluorescent polarization changes with time uniquely identifies the cell as being malignant.

BRIEF DESCRIPTION OF THE DRAWINGS

An embodiment of the invention is shown in the accompanying drawing.

DESCRIPTION OF THE PREFERRED EMBODIMENT

Referring now to FIG. 1, reference numeral 10 designates apparatus in accordance with the present invention for determining the normality of a population of mammalian cells on a cell-by-cell basis. Apparatus 10 comprises fluorescent microscope 11, which may be similar to a microscope shown in U.S. Pat. No. 3,860,813; microscope table 12; and table positioning mechanism 13 which may be of the type disclosed in U.S. Pat. Nos. 3,851,972 or 3,892,484. Microscope 11 includes a light source 14 for directing light along horizontal axis 15 toward a dichroic mirror 16 where such light is reflected along vertical axis 19 into a nonfluorescent microscope objective 17 from which it exits and is incident on sample slide 18 carried by table 12. The sample slide carries a population of treated cells deposited thereon as described below so that they can be examined one-at-a-time.

Microscope table 12 operatively supports slide 18 relative to the objective, and can be selectively displaced in a plane perpendicular to axis 19 in accordance with manual or automatic command signals applied to control 20 of mechanism 13. Control 20 selectively supplies pulses to X-stepping motor 21 and Y-stepping motor 22 in accordance with the command signals. Thus, table 12 can be selectively displaced in discrete steps in two dimensions to position any elemental area of the slide in operative relationship to the objective.

Light source 14 is preferably a high-pressure mercury lamp aligned with axis 15 for producing light having a component at 365 nm wavelength. Shutter 23, selectively positionable relative to axis 15, can be moved out of blocking relationship with lamp 14 by means of operator 24. Downstream of shutter 23 is a filter station at which a dual filter is located, one of the filters 25 being for visible light, and the other filter 26 passing light of a wavelength that will excite the fluorescent dye used to label the cells under investigation. For the dye DPH(1.6-diphenyl 1,3,5,-hexatriene), the preferred excitation wavelength if 365 nm.

Both filters are rigidly fixed together, and are movable as a unit operator 27. The dual filter has a first position at which visible filter 25 is aligned with axis 15, and an operative position at which filter 26 is aligned with the axis.

Downstream of the filter station is light chopper 28 comprising a disc 29 driven by motor 30 for periodically chopping the light passing the filter station. Disc 29 is provided with a plurality of apertures 31 so that light from lamp 14 intermittently passes along the optical axis 15 when motor 30 rotates disc 20. Beyond the chopper station is located a Glan-Thomson polarizer 32 for polarizing the light furnished to dichroic mirror 16. Finally, a field diaphragm 33 is interposed between polarizer 32 and the dichroic mirror for the purpose of controlling the illuminated area on the slide which can be limited to the size of a cell, or a part of a cell. By reason of the operation of polarizer 32 when filter 26 is aligned with the optical axis, the light incident on dichroic mirror 16 will have a wavelength of 365 nm and will be polarized. For reference purposes, the direction of polarization is shown at 34, this symbol indicating that the direction of polarization is perpendicular on the paper. Obviously, the direction of polarization is arbitrary with respect to the drawing.

The light, polarized as indicated, is reflected by the dichroic mirror through objective 17 and onto the sample carried on sample slide 18. Assuming that a single cell labelled with a lipid soluble fluorescent dye has been localized relative to objective 17, i.e., has been positioned directly beneath the objective by reason of the operation of the slide table positioning mechanism 13, the polarized light incident on the labelled cell will excite the cell causing the latter to fluoresce. Fluorescent light, at a wavelength dependent on the fluorescent dye used to label the cells under investigation, will be emitted by the excited cell. For the dye DPH, the fluorescence will be at 420 nm. Such fluorescence from the cell will enter objective 17 and pass upwardly along axis 19 through dichroic mirror 16 and through cut-off filter 35 which functions to eliminate specular reflections.

At set of prisms 36 is selectively movable into and out of alignment with axis 19. When positioned on the axis, the prisms direct fluorescent light into eyepiece 37. When the prisms are removed from the axis, all of the fluorescent light passes into a Walaston prism or polarizer 38 which divides the output of the microscope into two output channels 39A, 39B polarized at different angles. Specifically, and for the purposes of illustration only, the light passing through channel 39A is polarized in a direction perpendicular to the paper as indicated by symbol 40, while the light passing through channel 39B is polarized in a direction parallel to the paper as indicated by symbol 41. Note that light in channel 39A is polarized in a direction parallel to the polarization of the excitation light, and in channel 39B, the polarization is perpendicular to the polarization of the excitation light.

The state of polarization of the fluorescence emitted by an excited cell localized relative to objective 17 is determined by a measurement of the intensities of fluroescence polarized at orthogonal angles. Such measurement is preferably carried out of utilizing single-photon counting techniques. Accordingly, each channel contains a single-photon counting detector, such as a photomultiplier, designated 42A and 42B, respectively. A sheet polaraizer 43A, oriented to pass polarized light in the direction of polarization of channel 39A, is selectively located in front of detector 42A; and a sheet polarizer 43B oriented to pass light polarized in the direction of polarization of channel 39B is selectively located in front of detector 42B. The outputs of each of detectors 42A and 42B are connected to a utilization device 44, to which is also supplied a synchronizing line 45 connected to angular position detector 46 for the purpose of relating the instantaneous alignment of an opening 31 with axis 15 to the instantaneous output of the two detectors.

Because two output channels 39A and 39B are utilized, measurements of the intensities of fluorescence polarized in directions parallel to and perpendicular to the direction of polarization of the excitation beam can be carried out simultaneously, eliminating from the data the influence of fluctuations in the intensity of the excitation beam dependent on the fluorescent output. The provision of adjustable polarizers 43A and 43B in the two channels enables the absolute values of light intensities reaching each detector to be controlled by rotating the polarizers thereby compensating for inhomogeneities in the optical system with respect to the light polarization. As a consequence, the data obtained using the apparatus of the present invention accurately reflects the membrane fluidity of each cell and enables abnormal cells to be distinguished from normal cells on a cell-by-cell basis.

It also should be appreciated that some modifications of means for controlling the number of counts per photons reaching each of the channels may be performed. As an example they may comprise variable neutral density filters in front of each said detector or means for electronically controlling the duty cycle of data transfer from the detector to the utilization device.

By reason of the operation of chopper 28, the excitation light is periodically incident on a sample localized relative to objective 17. The chopping frequency is approximately 200 Hz; consequently, the fluorescent output passing into polarizer 38 has a period of about 5 msec with a 50% duty cycle. Each 2.5 msec burst of fluorescence is many times longer than the lifetime of the fluorescent dye used to label the cells under consideration. For DPH, the lifetime is of the order of 10 nsec.

During a measurment mode of operation of the instrument, counts produced by a detector 42A or 42B, during the time that an opening 31 is aligned with axis 15 (i.e., during a 2.5 msec interval that a cell is excited), are accumulated in a counter (not shown) associated with each detector and part of utilization device 44. Synchronization information is obtained from the output of detector 46. During the time that disc 29 blocks the excitation light in channel 15 (i.e., during a 2.5 msec interval), counts produced by the detectors due to noise are subtracted from their associated counters. In this manner, low frequency internal noise can be eliminated.

A measurement of the intensities of fluorescent polarization at mutually perpendicular angles can be carried out as follows:

Mode I Measurement — Preset total photon count.

In this mode, the sum of the counts produced in each channel is preset. If the fluorescence intensities polarized in directions parallel and perpendicular to the direction of the excitation beam are designated $I_1$ and $I_2$ respectively, then for a Mode I measurement, the accumulation of counts in the counters associated with detectors 42A and 42B is terminated when $I_1 + I_2$ equals the preset count.

Mode II Measurement — Preset time

In this mode, the outputs of detectors 42A and 42B are gated into their associated counters for a preselected period of time. At the end of the gating period, the contents of the counters are representative of the fluorescence intensity polarized parallel ($I_1$) and perpendicular ($I_2$) to the polarization excitation, respectively.

In describing the operation of the apparatus shown in the drawing, it will be assumed that the table positioning mechanism 13 has completed the indexing of table 12 such that the table is stationary relative to objective 17, and polarized light from source 14 is incident on a cell or a portion of a cell on sample slide 18. Consequently, the cell will produce some fluorescent output which will be detected by detectors 42A and 42B.

Regardless of which mode of measurement is being utilized, the quantities $I_1$ and $I_2$ will be available within a relatively short time, and in any event, in less than one second, after table 12 has come to a halt. Discriminator 47 of utilization apparatus 44 performs the operation ($I_1 + I_2$) and compares the result with a threshold representative of the sum of the intensities in the two channel when, in fact, a cell or a part of a cell is localized with respect to objective 17. If the threshold is exceeded, discriminator 47 produces an enable signal in line 48 which serves to start clock 49 which generates a predetermined program of gating and control pulses, and which also serves to disable control 20 and halt further indexing of table 12.

At the same time, the counters associated with detectors 42A and 42B are cleared for enabling the parameters $I_1$ and $I_2$ to be recalculated and furnished to the "P" calculator 50 which performs the operation $(I_1-I_2)/(I_1+I_2)$ thus defining an "instantaneous" state of polarization of the fluorescent output of a cell localized with respect to objective 17. While the term instantaneous is used to describe the state of polarization calculated at 50, it will be appreciated that a finite time is required to accumulate the counts by which $I_1$ and $I_2$ are measured, and the contents of the counters associated with the detectors represents the intensities at a particular point in time as measured from the time that excitation commenced.

Once the degree of fluorescent polarization has been computed, clock 49 opens gate 51 and transfers the contents of calculator 50 to the memory 52.

The above-described procedure is repeated after a predetermined period of time which can range from 5 to 30 seconds. When this is completed, memory 52 contains two P values obtained within the above mentioned period of excitation. Calculator 52 is then enabled for the purpose of comparing the values contained in the registers of memory 52 in order to determine the stability of the state of polarization.

The stability of the state of fluorescent polarization, in this case the degree of fluorescent polarization, indicative of the normality of a cell is determined experimentally. It has been found that the P value of DPH labeled normal lymphocytes (normal mouse cells) during a period of five seconds of excitation remained within the range 0.205±0.005, i.e., substantially constant. When the cells are normal cervical cells, a spectrum of P values is measured in the range 0.1 to 0.4 immediately after excitation. Thereafter, and during the next twelve seconds from the start of excitation, the P value remains substantially constant varying by less than 0.005. For malignant cells, the P value increases significantly within the same time scale.

For malignant lymphoma cells (mouse leukemia), the P values increase from 0.156±0.005 to 0.195±0.005 within 5 seconds. For human carcinogenous cervical cells, the P values increase by 0.020 or more.

If calculator 53 determines that the values of the degree of fluorescent polarization are within ±5%, the cell which has been localized with respect to objective 17 is considered as being normal enabling classification in this respect to be made; otherwise, the calculator 53 classifies the cell as being malignant.

The following may be helpful in understanding the observed phenomena. The membrane of a mammalian cell consists fundamentally of a lipid bilayer, composed of phospholipids and cholesterol in which membrane proteins are embedded. In order to examine the fluidity/rigidity nature of the lipid bilayer, a lipid soluble fluorescent probe such as DPH is added to a cell suspension in phosphate buffered saline and allowed to incubate for about an hour. The labeled cells are then deposited on a microscope slide and then illuminated by a fine beam of polarized ultraviolet light. The polarized light preferentially excites those fluorescent molecules whose absorption dipole happens to coincide with the direction of the electric vector of the excitation light. The Brownian motion at constant temperature of the fluorescent molecules causes a certain depolarization of the light emitted after de-excitation, such depolarization being measured by the degree of fluorescent polarization, P. The quantity P reflects the dynamics of the behaviour of the lipid bilayer (fluidity/rigidity) in the immediate surrounding of the fluorescent probe molecule. This P value, for normal cells, reflecting the local rigidity of the lipid regions, remains substantially constant as a function of time, reflecting constant rigidity.

The conclusion determined by the logic of calculator 53 is indicated by printer 54 which provides a visual display of whether the cell being examined is normal, abnormal or non-identified. Calculator 53, having reached a conclusion with respect to a cell under examination, then provides an "advanced order" to control 20 enabling the same and causing stepping motors 21 and 22 to index table 12 through a displacement equal to approximately two times the average cell size. When this index step is completed, the process described above is repeated with discriminator 47 determining whether a cell has been localized with respect to objective 17. If the threshold of discriminator 47 is not exceeded, control 20 is effective to index the table through another displacement of the type described above and the process is repeated. Eventually, another cell is localized with respect to the objective, and its normality is ascertained as previously described.

While the apparatus described above utilizes the state of fluorescent polarization in terms of the degree of fluorescent polarization, other combinations of the quantities $I_1$ and $I_2$ can be utilized if desired, if correlation is shown between normal and abnormal cells for such other combinations. Furthermore, the ratio of the quantities $I_1$ and $I_2$ may be of value in determining the normality of the cells of the population.

It is believed that the advantages and improved results furnished by the method and apparatus of the present invention are apparent from the foregoing description of the preferred embodiment of the invention. Various changes and modifications may be made without departing from the spirit and scope of the invention as sought to be defined in the claims that follow.

I claim:

1. A method for determining the normality of a biological cell that has been labeled with a lipid soluble fluorescent dye and excited with polarized light by utilizing the stability of the state of polarization of fluorescence emitted by the cell as a function of excitation time.

2. A method for determining the normality of biological cells comprising the steps of:
    (a) labeling the cells in a population with a lipid soluble fluorescent dye;
    (b) exciting a cell under consideration with polarized light; and
    (c) determining the state of polarization of fluorescence emitted by the cell under consideration as a function of excitation time.

3. A method according to claim 2 including the step of comparing the determined time-dependent state of polarization with a predetermined time-dependent state of polarization associated with a normal cell for determining the normality of the cell under consideration.

4. A method according to claim 2 wherein the degree of fluorescent polarization is determined as a function of excitation time by a plurality of sequential computations.

5. A method according to claim 2 including the steps of sequentially carrying out steps (b) and (c) with the cells in the population, and classifying the cells according to the time-wise stability of the state of polarization of fluorescence emitted by the cells.

6. Apparatus for determining the normality of the population of biological cells that have been labeled with a lipid soluble fluorescent dye comprising:
   (a) means for selectively exciting a cell in the population with polarized light;
   (b) means responsive to the fluorescence emitted by the cell for determining its state of polarization as a function of excitation time.

7. Apparatus according to claim 6 including means for comparing the determined time-dependent state of polarization with a predetermined time-dependent state of polarization associated with a normal cell.

8. Apparatus according to claim 6 wherein the means responsive to the fluorescence includes:
   (a) means for separating the light emitted by the cell into two channels polarized at different angles; and
   (b) means for measuring the light intensity in each channel as a function of time during which excitation occurs.

9. Apparatus in accordance with claim 8 wherein the polarization in the two channels is mutually perpendicular.

10. Apparatus for classifying biological cells comprising:
    (a) a fluorescent microscope having a light source for directing polarized light into an objective through a dichroic mirror which passes light picked up by the objective into an output path;
    (b) a microscope table operatively positioned relative to the objective for holding a slide on which are deposited cells labeled with a lipid soluble fluorescent dye;
    (c) means for selectively positioning the table in two directions relative to the objective;
    (d) means in the output path of the microscope for separating the light therein into two channels polarized at different angles; and
    (e) means for measuring $I_1$ and $I_2$, the intensities of light in the respective channels, and calculating P, repeatedly, over a predetermined time interval where $P = (I_1 - I_2) / (I_1 + I_2)$.

11. Apparatus according to claim 10 including means for determining the time-wise stability of P in said predetermined time interval.

12. Apparatus in accordance with claim 11 including means for classifying a cell as abnormal when the stability of P is less than a threshold.

13. Apparatus according to claim 12 including means for determining the time-wise stability of P for each cell.

14. Apparatus in accordance with claim 13 including means for classifying cells in the population according to the time-wise stability of P of each cell.

15. Apparatus according to claim 10 including means for causing the polarized light directed into the objective to be periodic, the period of the polarized light being much smaller than the predetermined time interval.

16. Apparatus according to claim 10 wherein the predetermined time is in the range 5 to 30 seconds.

17. Apparatus in accordance with claim 10 wherein the means for selectively positioning the table includes means for displacing the table until $I_1 + I_2$ exceeds a threshold, and holding the table fixed for said predetermined time interval whereby each cell in the population on the slide can be sequentially localized in operative association with the objection.

* * * * *